(12) United States Patent
Rea et al.

(10) Patent No.: US 7,575,593 B2
(45) Date of Patent: Aug. 18, 2009

(54) IMPLANTABLE DEVICE WITH RESERVOIRS FOR INCREASED DRUG LOADING

(75) Inventors: Susan Rea, Santa Rosa, CA (US); Jeff Allen, Santa Rosa, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 255 days.

(21) Appl. No.: 11/668,907

(22) Filed: Jan. 30, 2007

(65) Prior Publication Data

US 2008/0183281 A1    Jul. 31, 2008

(51) Int. Cl.
*A61F 2/06* (2006.01)
(52) U.S. Cl. .................... 623/1.42; 623/901
(58) Field of Classification Search ....... 623/1.11–1.48, 623/901
See application file for complete search history.

(56) References Cited

U.S. PATENT DOCUMENTS

| | | | | |
|---|---|---|---|---|
| 5,855,802 | A * | 1/1999 | Acciai et al. | 216/8 |
| 5,902,475 | A * | 5/1999 | Trozera et al. | 205/655 |
| 6,019,784 | A * | 2/2000 | Hines | 128/898 |
| 6,086,773 | A * | 7/2000 | Dufresne et al. | 216/8 |
| 6,537,459 | B1 | 3/2003 | Dufresne et al. | |
| 6,558,733 | B1 * | 5/2003 | Hossainy et al. | 427/2.24 |
| 6,709,379 | B1 | 3/2004 | Brandau et al. | |
| 6,740,114 | B2 * | 5/2004 | Burgermeister | 623/1.17 |
| 6,979,347 | B1 | 12/2005 | Wu et al. | |
| 6,998,060 | B2 * | 2/2006 | Tomonto | 216/8 |
| 7,041,130 | B2 * | 5/2006 | Santini et al. | 623/1.42 |
| 7,118,656 | B2 | 10/2006 | Roth | |
| 7,163,555 | B2 * | 1/2007 | Dinh | 623/1.42 |
| 2002/0038145 | A1 * | 3/2002 | Jang | 623/1.15 |
| 2004/0026359 | A1 | 2/2004 | Dufresne et al. | |
| 2005/0033412 | A1 | 2/2005 | Wu et al. | |

FOREIGN PATENT DOCUMENTS

| | | |
|---|---|---|
| EP | 0875218 | 11/1998 |
| WO | WO2006/029364 | 3/2006 |

OTHER PUBLICATIONS

Schneider, A., et al. "Surface Microstructuring of Biocompatible Bone Analogue Material HAPEX Using LIGA Technique and Embossing," Abstract.

* cited by examiner

*Primary Examiner*—Suzette J Gherbi

(57) ABSTRACT

A method of manufacturing a drug loaded stent includes applying a photo resistant coating to at least a portion of a stent framework and removing at least a portion of the photo resistant coating from the stent framework. The method further includes applying an etchant to at least a portion of the stent framework and forming a plurality undercut drug reservoirs in the stent framework based on applying the etchant. A stent for treating a vascular condition includes a stent framework, a plurality of undercut reservoirs formed within the stent framework and a therapeutic agent disposed within at least a portion of the plurality of undercut reservoirs.

17 Claims, 8 Drawing Sheets

330 FIG. 3
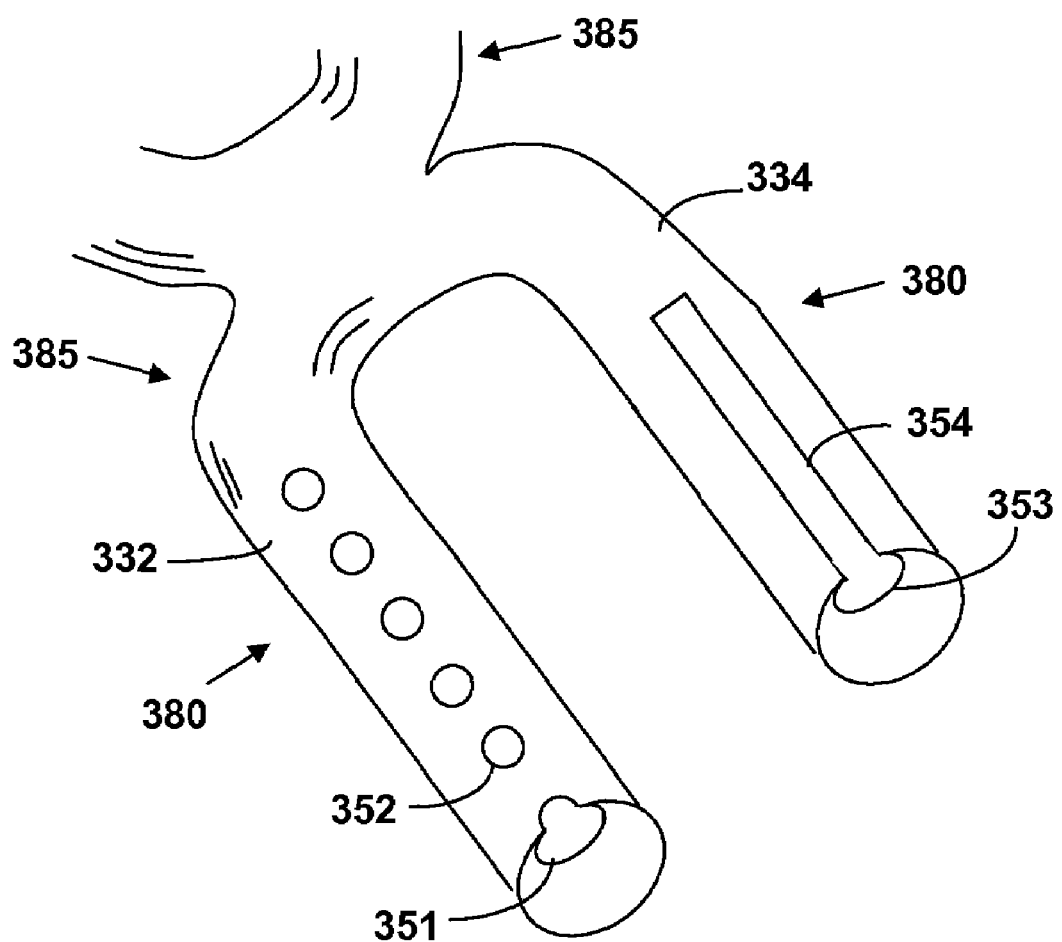

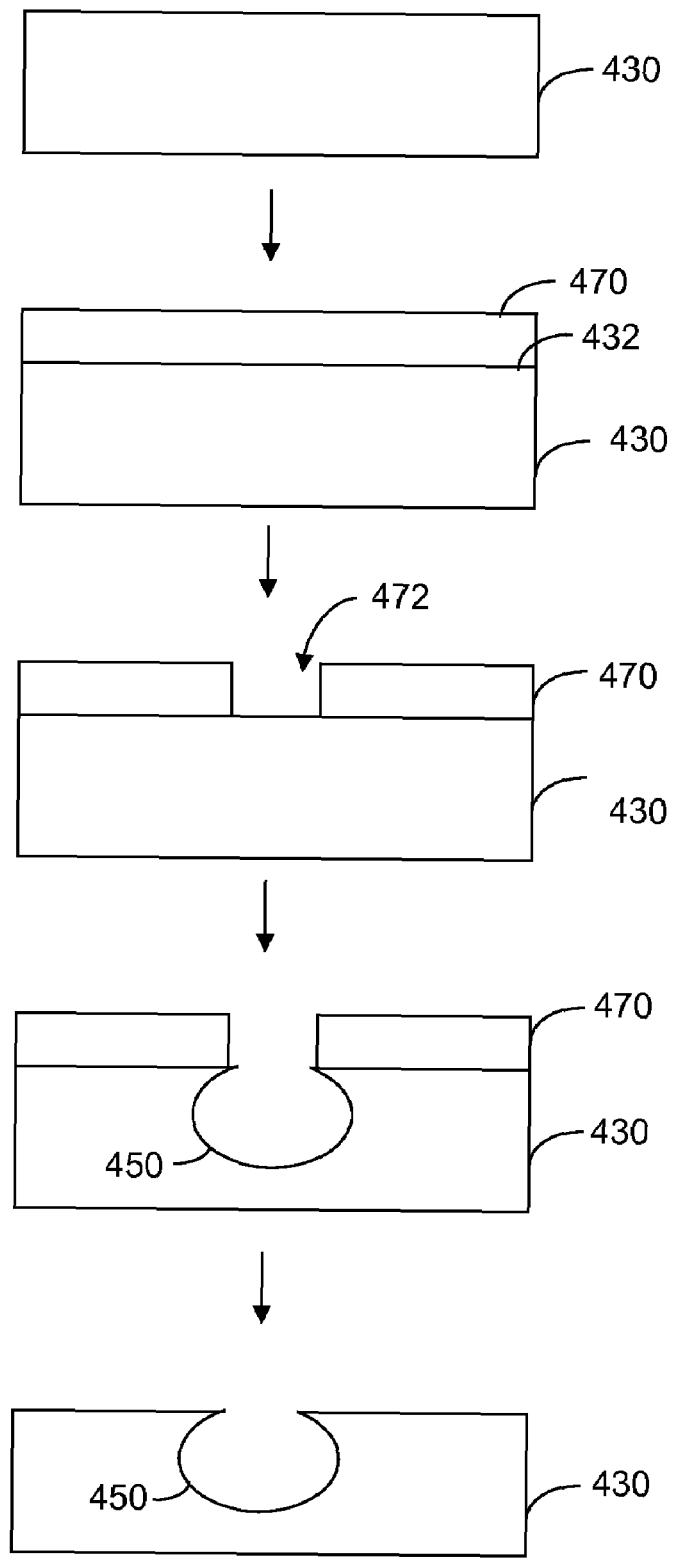

FIG. 5 <u>500</u>
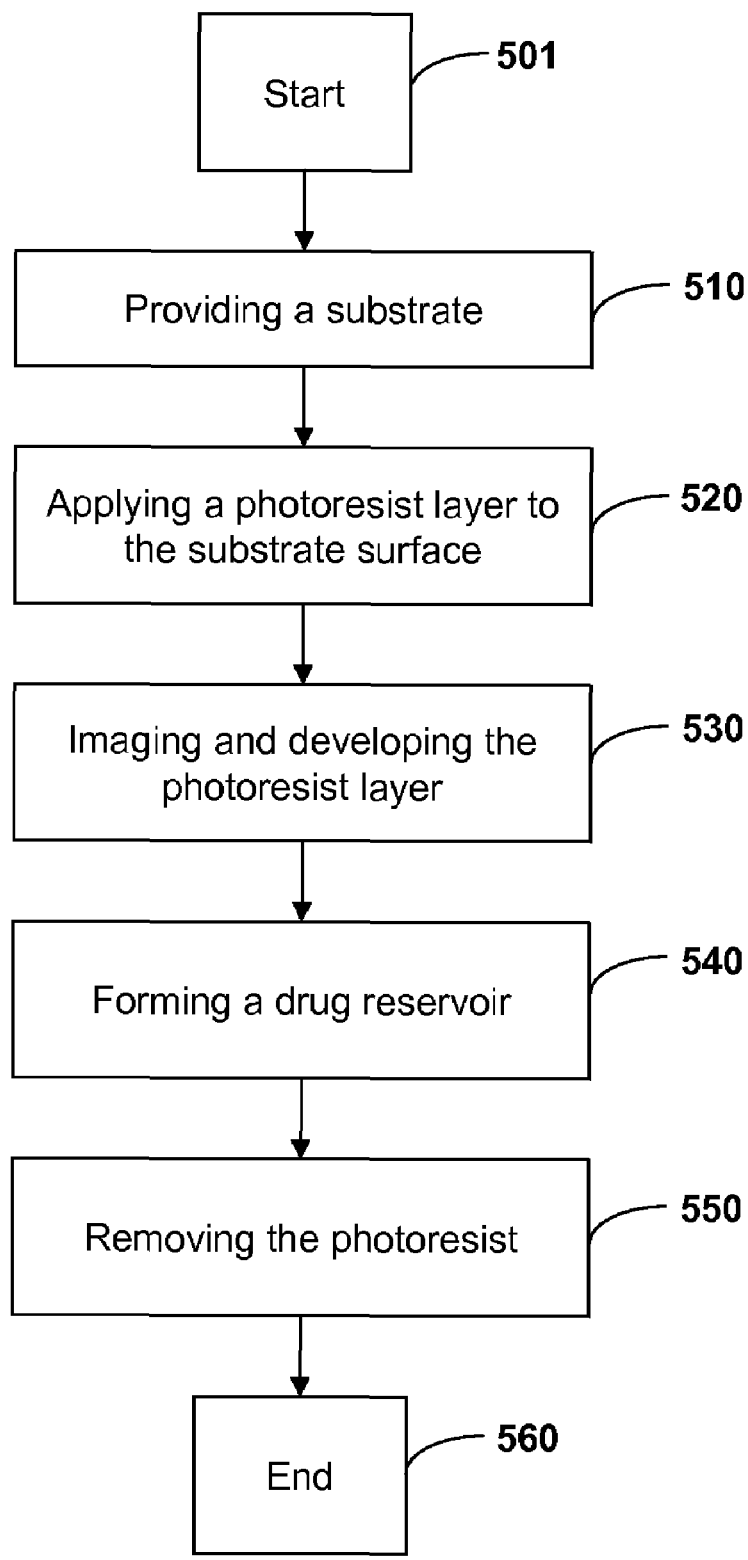

730 # FIG. 7
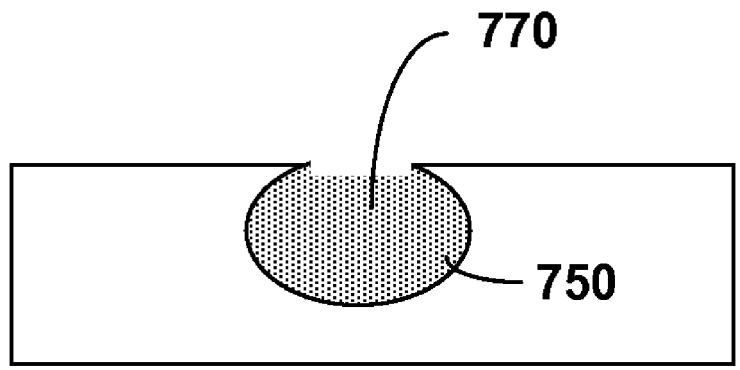
830 # FIG. 8
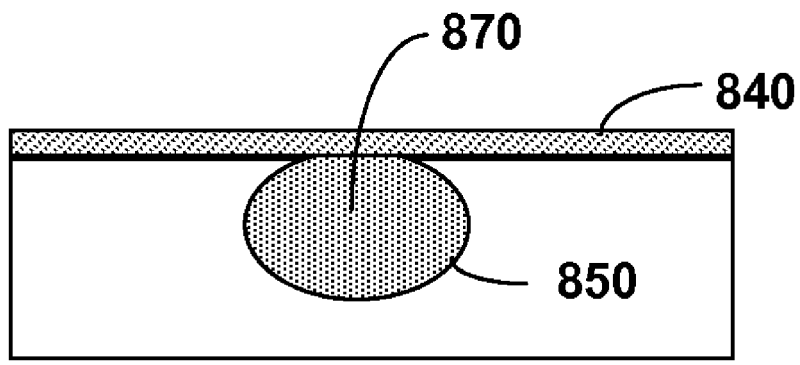

IMPLANTABLE DEVICE WITH RESERVOIRS FOR INCREASED DRUG LOADING

TECHNICAL FIELD

The technical field of this disclosure is medical implantable device coating methods, particularly, a system and method for providing an implantable device with reservoirs to increase the amount of therapeutic agent loaded into the implantable device.

BACKGROUND OF THE INVENTION

Wide ranges of medical treatments have been developed using implantable devices such as endoluminal prostheses, which are medical devices adapted for temporary or permanent implantation within a body lumen, including naturally occurring and artificially made lumens. Examples of lumens in which endoluminal prostheses may be implanted include arteries such as those located within coronary, mesentery, peripheral, or cerebral vasculature; veins; gastrointestinal tract; biliary tract; urethra; trachea; hepatic shunts; and fallopian tubes. Various types of endoluminal prostheses have also been developed with particular structure to modify the mechanics of the targeted luminal wall.

Stents are one example of an endoluminal prosthesis. Stents are generally cylindrical shaped devices that are radially expandable to hold open a segment of a blood vessel or other anatomical lumen after implantation into the body lumen. Various types of stents are in use, including balloon expandable and self-expanding stents. Balloon expandable stents generally are conveyed to the area to be treated on balloon catheters or other expandable devices. For insertion, the stent is positioned in a compressed configuration along a delivery device. The stent may be fixed to a balloon that is folded or otherwise wrapped about a guide catheter that is part of the delivery device. After the stent is positioned across a lesion, the stent is expanded by the delivery device. For a self-expanding stent, a sheath is retracted allowing expansion of the stent.

Stents are used in conjunction with balloon catheters in a variety of medical therapeutic applications including intravascular angioplasty. For example, a balloon catheter is inflated during PTCA (percutaneous transluminal coronary angioplasty) to dilate a stenotic blood vessel. The stenosis may be the result of a lesion such as a plaque or thrombus. After inflation, the pressurized balloon exerts a compressive force on the lesion thereby increasing the inner diameter of the affected vessel. The increased interior vessel diameter facilitates improved blood flow. Unfortunately, significant proportions of treated vessels re-narrow or collapse soon after the procedure.

To prevent acute vessel narrowing or collapse, short flexible cylinders, or stents, constructed of metal or various polymers are implanted within the vessel to maintain lumen diameter. The stents acts as a scaffold to support the lumen in an open position. Balloon-expandable stents are mounted on a collapsed balloon at a diameter smaller than when the stents are deployed. Stents can also be self-expanding, growing to a final diameter when deployed without mechanical assistance from a balloon or like device.

Stent insertion may cause undesirable reactions such as inflammation, infection, thrombosis, and proliferation of cell growth that occludes the passageway.

To reduce restenosis stents have been developed with coatings to deliver drugs or other therapeutic solutions. Once the stent is positioned in a target site, these coatings offer long-term treatment from the drug by a controlled release of a specific amount of the drug from the surface of the stent. The rate of release depends upon the chemical and or biological composition of the drug and the amount of the drug depends upon the total depth and depth consistency of the drug coating layer on the stent surface. It has been discovered that methods of loading drugs onto implantable devices may be deficient in their current drug-loading and drug-delivery characteristics. In particular, the amount or volume of the drug capable of being delivered to the target site may be insufficient due to the limited surface areas on the stent and the control of the rate of elution is limited by the chemical characteristics of the drug. In addition, during delivery of the stent, any coating exposed to the body lumen can lose a portion of the coating during delivery, either as a result of blood flow over the surface, or by contacting the vessel tissue prior to delivery to the target site. Furthermore, the use of a polymer matrix to control the release of the drug has been shown to lead to inflammatory response and may be linked to the occurrence of late thrombosis within the stent. Reducing or eliminating the amount of polymer required to achieve a desired controlled drug release would therefore be of great benefit.

To increase the amount of the drug that may be deposited on the surface of the stent, the surface of the stent framework has been modified. Such modifications may be the formation of openings in the stent surface to hold more of the drug. For example, reservoirs can be formed into the surface of the stent with the use of lasers or by dimpling the surface.

One problem that has arisen with drug reservoirs within implantable devices is that after implantation the rate of release of the drug from the reservoir is hard to control due to the size of the opening through which the drug is released.

It would be desirable to have an implantable device with drug reservoirs that would overcome these and other disadvantages.

SUMMARY OF THE INVENTION

One aspect of the present invention provides a method of manufacturing a drug loaded stent. The method includes applying a photo resistant coating to at least a portion of a stent framework and removing at least a portion of the photo resistant coating from the stent framework. The method further includes applying an etchant to at least a portion of the stent framework and forming a plurality of undercut drug reservoirs in the stent framework based on applying the etchant.

Another aspect of the present invention provides a system for treating a vascular condition. The system includes a catheter and a stent disposed on the catheter, the stent including a stent framework. The system further includes a plurality of undercut reservoirs formed within the stent framework and a therapeutic agent loaded within the reservoirs.

Another aspect of the present invention provides a stent for treating a vascular condition. The stent includes a stent framework, a plurality of undercut reservoirs formed within the stent framework and a therapeutic agent disposed within at least a portion of the plurality of undercut reservoirs.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

FIG. 3 is a cross-sectional perspective view of a stent framework having drug reservoirs made in accordance with the present invention;

FIG. 4 is an illustration of a method for forming drug reservoirs on a stent, in accordance with one embodiment of the present invention;

FIG. 5 is a flow diagram of a method for forming drug reservoirs on a stent, in accordance with one embodiment of the present invention;

FIG. 7 is a cross section of a drug loaded drug reservoir formed within a stent framework, in accordance with one aspect of the present invention;

FIG. 8 is a cross section of a drug loaded drug reservoir formed within a coated stent framework, in accordance with one aspect of the present invention.

DETAILED DESCRIPTION

The invention will now be described by reference to the drawings wherein like numbers refer to like structures.

Figure 1:
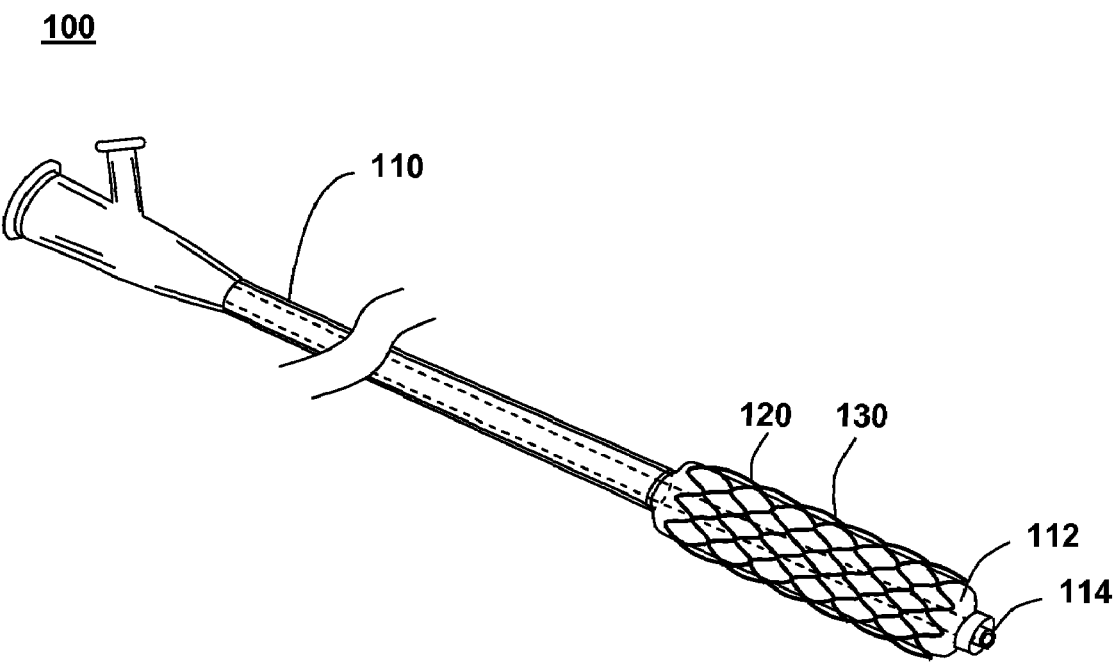
FIG. 1 is an illustration of a system for treating a vascular condition including a stent coupled to a catheter, in accordance with one embodiment of the present invention.

FIG. 1 shows an illustration of a system for treating a vascular condition, comprising a stent coupled to a catheter, in accordance with one embodiment of the present invention at 100. Stent with catheter 100 includes a stent 120 coupled to a delivery catheter 110. Stent 120 includes a stent framework 130. Stent framework 130 includes a plurality of drug reservoirs disposed within an outer surface of the stent framework. A therapeutic drug is disposed within the drug reservoirs. The drug reservoirs, in one embodiment, are pores. In another embodiment, the drug reservoirs are channels.

Insertion of stent 120 into a vessel in the body helps treat, for example, heart disease, various cardiovascular ailments, and other vascular conditions. Catheter-deployed stent 120 typically is used to treat one or more blockages, occlusions, stenoses, or diseased regions in the coronary artery, femoral artery, peripheral arteries, and other arteries in the body. Treatment of vascular conditions may include the prevention or correction of various ailments and deficiencies associated with the cardiovascular system, the cerebrovascular system, urinogenital systems, biliary conduits, abdominal passageways and other biological vessels within the body.

The stent framework comprises a metal, polymer, or metal alloy. Appropriate metal alloys include, but are not limited to, magnesium alloy, cobalt-chromium, MP35N, nitinol, titanium, stainless steel or other appropriate materials.

Catheter 110 of an exemplary embodiment of the present invention includes a balloon 112 that expands and deploys the stent within a vessel of the body. After positioning stent 120 within the vessel with the assistance of a guide wire traversing through a guide wire lumen 114 inside catheter 110, balloon 112 is inflated by pressurizing a fluid such as a contrast fluid or saline solution that fills a tube inside catheter 110 and balloon 112. Stent 120 is expanded until a desired diameter is reached, and then the contrast fluid is depressurized or pumped out, separating balloon 112 from stent 120 and leaving the stent 120 deployed in the vessel of the body. Alternately, catheter 110 may include a sheath that retracts to allow expansion of a self-expanding version of stent 120.

Figure 2:
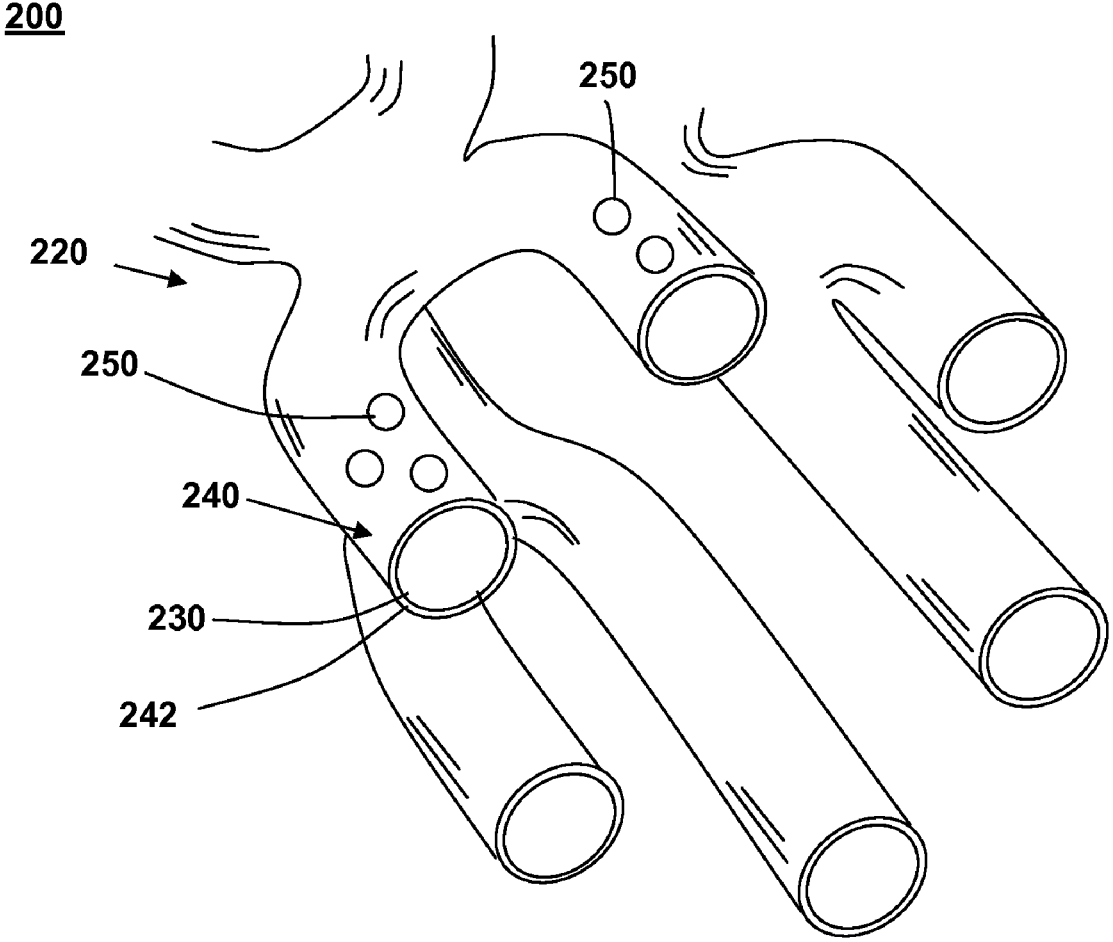
FIG. 2 is a cross-sectional perspective view of a coated stent framework, in accordance with one embodiment of the present invention.

FIG. 2 illustrates a cross-sectional perspective view of a stent, in accordance with one embodiment of the present invention at 200. Stent 220 includes a stent framework 230.

Stent framework 230 comprises any appropriate material, such as a polymer or a metal. For example, stent framework 230 may comprise a metallic base formed of magnesium, cobalt-chromium, stainless steel, nitinol, tantalum, MP35N alloy, platinum, titanium, a chromium-based alloy, a suitable biocompatible alloy, a suitable biocompatible material, a biocompatible polymer, or a combination thereof.

In one embodiment, a drug coating 240 is disposed on stent framework 230. In certain embodiments, drug coating 240 includes at least one drug layer 242. For example, drug layer 242 includes at least a first therapeutic agent. In one embodiment, the drug layer 242 is applied by spraying. In other embodiments, drug layer 242 is applied using another appropriate technique, such as vacuum deposition, dipping, or the like.

Although illustrated with one drug layer, multiple drug layers may be disposed on stent framework 230. For example, ten layers 0.1 micrometers thick, can be disposed on stent framework 230 to produce a one-micrometer thick coating. In another example, twenty layers 0.5 micrometers thick, can be disposed on stent framework 230 to produce a ten-micrometer thick coating. The drug layers need not be the same thickness, and the thickness of each may be varied throughout drug coating 240. In one example, at least one drug layer 242 is applied to an outer surface of the stent framework. The drug layer can comprise a first therapeutic agent such as camptothecin, rapamycin, a rapamycin derivative, or a rapamycin analog. Drug layer 242 may comprise more than one therapeutic agent.

Stent 220 also includes a plurality of drug reservoirs 250. Drug reservoirs 250 are disposed within the surface of the stent. As shown in FIG. 2, drug reservoirs 250 may be disposed within stent framework in a myriad of patterns. Drug reservoirs may be formed in various shapes such as, for example, spherical, oblong, ovoid and elongated. FIG. 3 illustrates a stent framework 330 with a plurality of ovoid drug reservoirs 351 having circular openings 352 disposed along stent framework strut 332 and an elongated drug reservoir 353 having a rectangular opening 354 disposed along stent framework strut 334.

Drug reservoirs may be formed at any place within the stent framework based on the particular application of the stent. In one embodiment, drug reservoirs are formed in the outer surface of the stent framework, the outer surface being that surface that contacts the wall of the vessel into which the device is implanted. In other embodiments, drug reservoirs are formed in the inner surface of the stent framework. In yet other embodiments, drug reservoirs are formed in both outer and inner surfaces of the stent framework. Another consideration for placement of drug reservoirs is the amount of strain the stent framework endures during manufacture and implantation. A stent framework has areas that undergo high levels of mechanical stress and/or strain and areas that undergo low levels of mechanical stress and/or strain. High strain areas are those areas, such as crown portions 385, which deform when placed (crimped) on the delivery catheter and when expanded during implantation. Low strain areas, such as elongated struts 380, undergo significantly less deformation when placed on the delivery catheter and when implanted. In one embodiment, the number of drug reservoirs in a given portion of the stent framework is inversely proportional to the amount of strain the given area undergoes. For example, in areas of low strain a higher concentration of drug reservoirs are placed as compared to an adjacent area of high strain where few if any drug reservoirs are placed. In another embodiment, drug reservoirs are only placed in areas of low strain.

FIG. 4 is a diagram illustrating a process 400 for forming undercut drug reservoirs on a stent, in accordance with the present invention. FIG. 5 illustrates a flow chart of a method 500 of performing the process 400 for forming undercut drug reservoirs on a stent, in accordance with the present invention. Method 500 starts at 501.

At step 510, a substrate 430 into which the undercut drug reservoirs are to be formed is provided. In one embodiment, substrate 430 comprises a stent framework of a stent. Substrate 430 may be any other implantable device as are known to those with skill in the art. Substrate 430 is composed of any appropriate material, such as a polymer or a metal. Substrate 430 may be, for example, a metallic base formed of magnesium, cobalt-chromium, stainless steel, nitinol, tantalum, MP35N alloy, platinum, titanium, a chromium-based alloy, a suitable biocompatible alloy, a suitable biocompatible material, a biocompatible polymer, or a combination thereof. In one embodiment, the surface of substrate 430 is cleaned before moving on to step 520. Cleaning substrate 430 removes oils and other contaminants that may interfere with the photoresist process.

At step 520, a layer of photoresist material 470 is applied to a surface 432 of the provided substrate 430. The photoresist layer may be applied by dipping, by spraying or by any other method known to those with skill in the art. The thickness of the photoresist layer applied to the substrate may be determined based on several factors. These factors include, size of desired drug reservoir, concentration of the developing solvent, concentration of etchant solution and the solution resistance of the photoresist material. The thickness of the photoresist layer may also be determined based on the length of time the developing solution and/or the etchant solution remains on the substrate/photoresist layers. The thickness of the photoresist layer may be in the range of 5 to 300 micrometers. At step 530, the photoresist layer is imaged and developed to remove the photoresist coating in areas 472 corresponding to the desired drug reservoir(s). Those with skill in the art will appreciate that the method of exposing the desired area for etching may comprise a negative-acting or a positive-acting photoresist coating procedure as are well known in the art.

Next, at step 540, at least one undercut drug reservoir 450 is formed in the substrate surface. The undercut drug reservoir 450 is formed by chemical etching. At step 540, an etchant solution is applied to the exposed areas 472 of the substrate. The etchant solution may include any chemical suitable for dissolving the substrate to which it is applied. Suitable etchants include, but are not limited to, hydrofluoric acid, nitric acid, ammonium difluoride, ferric chloride and hydrochloric acid solutions. The chemical etchant solution may be applied by dipping, spraying or by any other method known to those with skill in the art. The chemical etchant solution may be in contact with the substrate for a predetermined length of time based on factors such as, for example, the size of the desired undercut drug reservoir, the strength of the etchant solution and the type of substrate material. In an example, where the substrate contains nickel, the etchant solution may comprise a relatively strong ferric chloride solution. Potassium hydroxide, tetramethylammonium hydroxide, ammonia persulfate, ammonia and hydrofluoric acid are also common etchants that may be used with metal substrates. The chemical etching solution is rinsed away or neutralized upon completion of the formation of the desired undercut drug reservoir.

At step 550, the remaining photoresist layer is removed. The remaining photoresist may be removed with a suitable corresponding solvent as are well known to those with skill in the art. In an example, the remaining photoresist layer is removed with an organic solvent such as isopropanol. Method 500 ends at step 560.

Figure 6A:
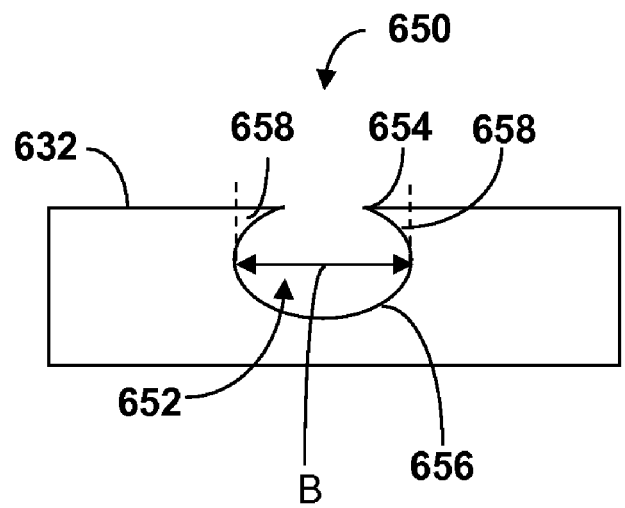
FIG. 6 is a cross section of a drug reservoir formed within a stent framework, in accordance with one aspect of the present invention.
Figure 6B:
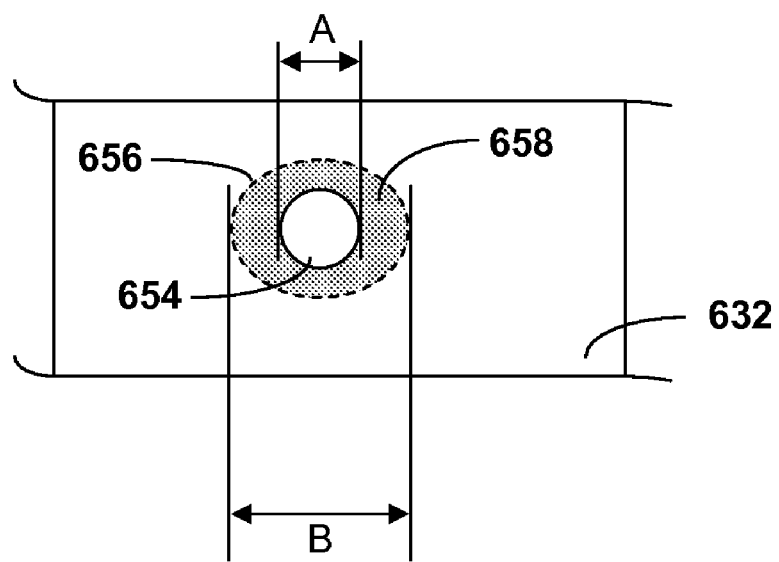

FIG. 6A illustrates a cross-sectional view of an undercut drug depot 650 made in accordance with the present invention. FIG. 6B illustrates a top view of a portion of a stent framework having an undercut drug depot 650 shown in FIG. 6A. Undercut drug depot 650 may be manufactured according to method 500 illustrated in FIG. 5.

Referring to FIGS. 6A and 6B, undercut drug depot 650 comprises a surface opening 654 and a chamber 652 defined by depot wall 656. Stent framework 630 includes an undercut region 658, represented as a shaded portion in FIG. 6B. Undercut region 658 is defined by drug depot wall 656 and surface opening 654. Drug depot surface opening 654 is located at the surface 632 of stent framework 630. Surface opening 654 has a first width, width A, defined by stent surface 632. Drug depot chamber 652 comprises a chamber recessed from the stent surface 632. Chamber 652 has a second width, width B, which is recessed from the stent framework surface. The width of the first width is less than the width of the second width. In one embodiment, the first width is less than half of the width of the second width. In another embodiment, the second width dimension is at least twice the first width dimension. Many ratios are possible, for example, the first width may be 1 µm while the second width is 3 µm, or the first width may be 10 µm while the second width is 15 µm. The greater the difference between the first and second width the greater the retention effect on drug release will be. In particular, smaller values for the first width will restrict the release rate of the drug.

FIG. 7 illustrates a cross-section of a stent strut 730 having an undercut drug depot 750. Undercut drug depot 750 may be manufactured according to method 500 illustrated in FIG. 5. FIG. 7 illustrates a therapeutic agent 770 disposed within undercut drug depot 750. Therapeutic agent 770 may be loaded into undercut drug depot 750 by dipping, spraying, vacuum deposition, particulate leaching, emulsion freeze drying, supercritical fluid treatment or brushing. In a dipping approach, ultrasonication of the solution containing the drug improves uptake into the undercut drug depot 750. Therapeutic agent 770 may include one or more therapeutic substances. In certain embodiments, the therapeutic substance is a drug such as an antirestenotic agent such as rapamycin, a rapamycin derivative, or a rapamycin analog to prevent or reduce the recurrence of narrowing and blockage of the bodily vessel. The therapeutic substance may also be an anti-cancer drug such as camptothecin or other topoisomerase inhibitor, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, an organic drug, a pharmaceutical compound, a recombinant DNA product, a recombinant RNA product, a collagen, a collagenic derivative, a protein, a protein analog, a saccharide, a saccharide derivative, a bioactive agent, a pharmaceutical drug, or a combination thereof.

FIG. 8 illustrates a cross-section of a stent strut 830 having an undercut drug depot 850. Undercut drug depot 850 may be manufactured according to method 500 illustrated in FIG. 5. FIG. 8 illustrates a therapeutic agent 870 disposed within undercut drug depot 850. Therapeutic agent 870 may be disposed within undercut drug depot by the same or similar procedure as described above for loading undercut drug depot 750. Therapeutic agent 870 may be the same as those listed above for therapeutic agent 770. Stent strut 830 also includes a therapeutic coating 840. Therapeutic coating 840 may be applied by any appropriate technique, including dipping, spraying, sputtering, vacuum deposition, or the like. Therapeutic coating 840 may include a therapeutic agent that is the same as or similar to therapeutic agent 870. In another embodiment, therapeutic agent 870 comprises a first drug and therapeutic agent 840 comprises a second drug different from the first drug disposed within the undercut drug depot 850.

Figure 9:
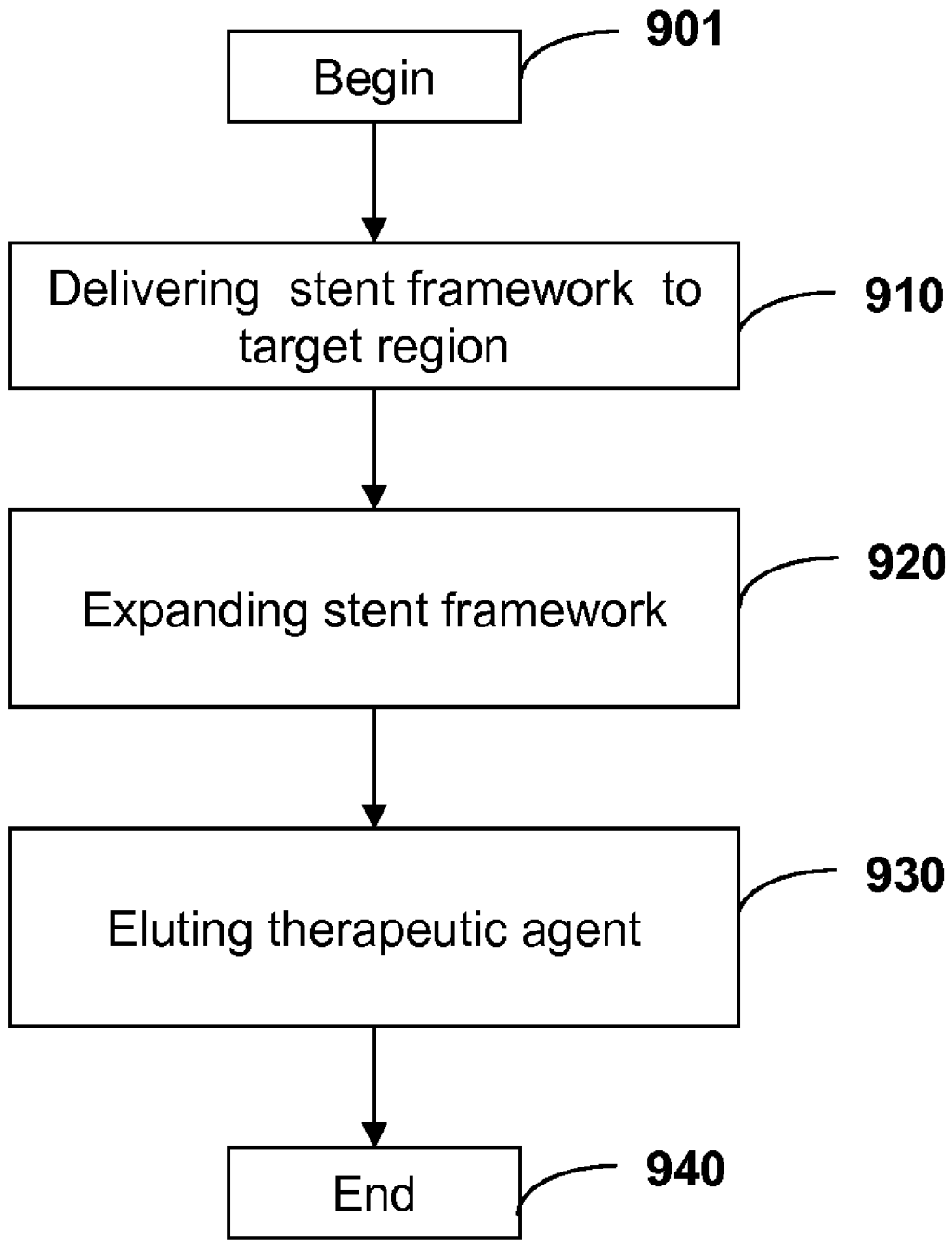
FIG. 9 is a flow diagram of a method for treating a vascular condition, in accordance with one embodiment of the present invention.

FIG. 9 shows a flow diagram of a method 900 for treating a vascular condition, in accordance with one embodiment of the present invention. Method 900 begins at 901. Method 900 continues by delivering a stent framework with a plurality of undercut drug depots to a target region of a vessel at step 910. The delivered stent can be any variety of implantable device capable of having undercut therapeutic drug depots and optionally carrying a therapeutic coating known in the art and being expandable with a balloon or self expandable to hold open a lumen.

Once delivered, the stent framework is expanded into contact with the treatment site, step 920. Once the stent is expanded, at least a portion of the therapeutic agent is eluted from the coating and/or the drug depot, step 930.

The undercut drug depots may be as described and illustrated above in FIGS. 2-8. Those skilled in the art will appreciate that the undercut drug depots can have particular depths and geometries as desired for a particular application. The depths and geometries can be selected to allow a particular release characteristic for a therapeutic agent, for example. In addition, the shape or geometry of the undercut drug depots can be controlled to affect release characteristics. Additionally, the geometry of each undercut drug depots can vary along the span of a single stent to provide for a plurality of release characteristics.

In one embodiment, the therapeutic agent disposed within the undercut drug depot includes a therapeutic drug without a polymer carrier. Suitable therapeutic agents include, but are not limited to, antiangiogenesis agents, antiendothelin agents, antimitogenic factors, antioxidants, antiplatelet agents, antiproliferative agents, antisense oligonucleotides, antithrombogenic agents, calcium channel blockers, clot dissolving enzymes, growth factors, growth factor inhibitors, nitrates, nitric oxide releasing agents, vasodilators, virus-mediated gene transfer agents, agents having a desirable therapeutic application, combinations of the above, and the like. Specific example of therapeutic agents include abciximab, angiopeptin, colchicine, eptifibatide, heparin, hirudin, lovastatin, methotrexate, rapamycin, Resten-NG (AVI-4126) antisense compound, streptokinase, taxol, ticlopidine, tissue plasminogen activator, trapidil, urokinase, and growth factors VEGF, TGF-beta, IGF, PDGF, and FGF.

In another embodiment, the therapeutic agent disposed within the undercut drug depot is a therapeutic drug mixed with a polymer carrier. Suitable polymers include, but are not limited to, urethane, polyester, epoxy, polycaprolactone (PCL), polymethylmethacrylate (PMMA), PEVA, PBMA, PHEMA, PEVAc, PVAc, Poly N-Vinyl pyrrolidone, Poly (ethylene-vinyl alcohol), combinations of the above, and the like. In one embodiment, the therapeutic agent may be removed from the exterior surface of the stent so that the polymer is only found in the undercut drug depots. The coating can be removed mechanically or chemically.

For application into the undercut drug depot and for coating the stent surface, the therapeutic agent can be mixed with a solvent to form a therapeutic solution. Suitable solvents include, but are not limited to, acetone, ethyl acetate, tetrahydrofuran (THF), chloroform, N-methylpyrrolidone (NMP), combinations of the above, and the like. Method 900 ends at 940.

It is important to note that this disclosure and illustrations illustrate specific applications and embodiments of the present invention, and are not intended to limit the scope of the present disclosure or claims to that which is presented therein. Upon reading the specification and reviewing the drawings hereof, it will become immediately obvious to those skilled in the art that many other embodiments of the present invention are possible, and that such embodiments are contemplated and fall within the scope of the presently claimed invention.

While specific embodiments of the invention are disclosed herein, various changes and modifications can be made without departing from the spirit and scope of the invention. The scope of the invention is indicated in the appended claims, and all changes that come within the meaning and range of equivalents are intended to be embraced therein.

The invention claimed is:

1. A method of manufacturing a drug loaded stent, the method comprising:
    applying a photo resistant coating to at least a portion of a stent framework;
    removing at least a portion of the photo resistant coating from the stent framework,
    applying an etchant to at least a portion of the stent framework; and
    forming a plurality undercut drug reservoirs in the stent framework based on the etchant application,
    wherein a first portion of the stent framework includes at least one drug reservoir comprising a pore and a second portion of the stent framework includes at least one drug reservoir comprising an elongated channel, the elongated channel spaced apart from the at least one pore.

2. The method of claim 1 wherein the drug reservoir includes a first width at a surface of the stent framework and a second width recessed from the surface of the stent framework, the first width being narrower than the second width.

3. The method of claim 1 further comprising:
    loading at least one of the undercut drug reservoirs with a first therapeutic agent.

4. The method of claim 3 wherein the first therapeutic agent is the same as the second therapeutic agent.

5. The method of claim 3 wherein the first therapeutic agent comprises a drug selected from the group consisting of antiangiogenesis agents, antiendothelin agents, antimitogenic factors, antioxidants, antiplatelet agents, antiproliferative agents, antisense oligonucleotides, antithrombogenic agents, calcium channel blockers, clot dissolving enzymes, growth factors, growth factor inhibitors, nitrates, nitric oxide releasing agents, vasodilators, virus-mediated gene transfer agents.

6. The method of claim 3 further comprising:
    coating at least a portion of the stent framework with a second therapeutic agent.

7. The method of claim 3 wherein the first therapeutic agent is different than the second therapeutic agent.

8. The method of claim 6 wherein the second therapeutic agent comprises a drug selected from the group consisting of antiangiogenesis agents, antiendothelin agents, antimitogenic factors, antioxidants, antiplatelet agents, antiproliferative agents, antisense oligonucleotides, antithrombogenic agents, calcium channel blockers, clot dissolving enzymes, growth factors, growth factor inhibitors, nitrates, nitric oxide releasing agents, vasodilators, virus-mediated gene transfer agents.

9. A system for treating a vascular condition, comprising:
a catheter;
a stent disposed on the catheter, the stent including a stent framework including a plurality of undercut reservoirs formed therein, wherein a first portion of the stent framework includes at least one drug reservoir comprising a pore and a second portion of the stent framework includes at least one drug reservoir comprising an elongated channel, the elongated channel spaced apart from the at least one pore; and
at least one therapeutic agent loaded within the reservoirs.

10. The system of claim 9 wherein the undercut reservoirs include an undercut portion of the stent framework surface, the undercut portion defined by a perimeter of the reservoir opening and an outer wall of the chamber.

11. The system of claim 10 wherein the reservoir opening has a first width and the chamber has a second width, the first width less than the second width.

12. The system of claim 11 wherein the second width is at least twice the first width.

13. The system of claim 9 wherein the therapeutic agent loaded within the undercut drug reservoirs comprises a drug selected from the group consisting of antiangiogenesis agents, antiendothelin agents, antimitogenic factors, antioxidants, antiplatelet agents, antiproliferative agents, antisense oligonucleotides, antithrombogenic agents, calcium channel blockers, clot dissolving enzymes, growth factors, growth factor inhibitors, nitrates, nitric oxide releasing agents, vasodilators, virus-mediated gene transfer agents.

14. A stent for treating a vascular condition, the stent comprising
a stent framework;
a plurality of undercut reservoirs formed within the stent framework, wherein a first portion of the stent framework includes at least one drug reservoir comprising a pore and a second portion of the stent framework includes at least one drug reservoir comprising an elongated channel, the elongated channel spaced apart from the at least one pore; and
a therapeutic agent disposed within at least a portion of the plurality of undercut reservoirs.

15. The stent of claim 14 further comprising:
a therapeutic coating disposed on at least a portion of the stent framework.

16. The stent of claim 15 wherein the reservoir opening has a first width and the reservoir chamber has a second width, and wherein the first width is less than the second width.

17. The stent of claim 14 wherein the undercut reservoirs include an undercut portion of the stent framework surface, the undercut portion defined by a perimeter of the reservoir opening and an outer wall of a reservoir chamber.

* * * * *